(12) United States Patent
Rowe

(10) Patent No.: US 12,130,276 B2
(45) Date of Patent: Oct. 29, 2024

(54) PREDICTED BIAS CORRECTION FOR A GAS EXTRACTOR AND FLUID SAMPLING SYSTEM

(71) Applicant: Halliburton Energy Services, Inc., Houston, TX (US)

(72) Inventor: Mathew Dennis Rowe, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 359 days.

(21) Appl. No.: 17/746,302

(22) Filed: May 17, 2022

(65) Prior Publication Data
US 2023/0374902 A1    Nov. 23, 2023

(51) Int. Cl.
| | |
|---|---|
| G01N 33/28 | (2006.01) |
| E21B 43/12 | (2006.01) |
| E21B 47/12 | (2012.01) |
| G01N 1/22 | (2006.01) |
| G01N 30/88 | (2006.01) |
| E21B 21/01 | (2006.01) |
| E21B 21/06 | (2006.01) |

(52) U.S. Cl.
CPC ....... *G01N 33/2841* (2013.01); *E21B 43/126* (2013.01); *E21B 47/138* (2020.05); *G01N 1/2294* (2013.01); *G01N 30/88* (2013.01); *G01N 33/2823* (2013.01); *E21B 21/01* (2013.01); *E21B 21/063* (2013.01); *G01N 2030/8854* (2013.01)

(58) Field of Classification Search
USPC .......................................................... 702/30
See application file for complete search history.

(56) References Cited

U.S. PATENT DOCUMENTS

| | | |
|---|---|---|
| 6,389,878 B1 | 5/2002 | Zamfes |
| 10,962,464 B2 | 3/2021 | Calleri |
| 2011/0219853 A1 | 9/2011 | Henderson |
| 2014/0166361 A1* | 6/2014 | Jamison ............... E21B 44/00 175/24 |

(Continued)

FOREIGN PATENT DOCUMENTS

WO    2019143362 A1    7/2019

OTHER PUBLICATIONS

Halliburton Energy Services, Inc., International Search Report and Written Opinion, PCT/US2022/029609, Feb. 14, 2023, 10 pages.

*Primary Examiner* — Paul D Lee
(74) *Attorney, Agent, or Firm* — Kilpatrick Townsend & Stockton LLP

(57) ABSTRACT

A system can flush a drilling fluid sample with a hydrocarbon blend, which includes a determined concentration of at least one chemical species to generate a flushed drilling fluid sample. The system can extract a dissolved gas from the flushed drilling fluid sample. The system can determine a concentration over time of at least one chemical species of the dissolved gas. The system can generate an area per concentration curve based on the concentration over time of the at least one chemical species. The system can determine at least one concentration value of the at least one chemical species. The system can modify the at least one concentration value based on the area per concentration curve. The system can then correct bias caused by the gas extractor and fluid sampling system.

20 Claims, 14 Drawing Sheets

(56) References Cited

U.S. PATENT DOCUMENTS

| | | | |
|---|---|---|---|
| 2016/0160641 A1* | 6/2016 | Rowe | E21B 49/086 |
| | | | 250/288 |
| 2018/0016857 A1 | 1/2018 | Shekhar et al. | |
| 2020/0256188 A1 | 8/2020 | Rowe | |
| 2022/0186616 A1* | 6/2022 | Shekhar | G01N 33/2823 |

* cited by examiner

PREDICTED BIAS CORRECTION FOR A GAS EXTRACTOR AND FLUID SAMPLING SYSTEM

TECHNICAL FIELD

The present disclosure relates generally to wellbore drilling operations and, more particularly (although not necessarily exclusively), to predicted bias correction for a gas extractor and fluid sampling system for drilling operations.

BACKGROUND

During the drilling of subterranean wells, a fluid may circulate through a fluid circulation system that includes a drilling rig and fluid treatment and storage equipment located at or near a surface of a well. The fluid may be pumped by a fluid pump through an interior passage of a drill string, through a drill bit, and back to the surface through an annulus between a wellbore and the drill string. As the well is drilled, fluids, including gases and liquids from the formation, may be released and captured as the fluid is circulated. In some instances, the gases may be wholly or partially extracted from the fluid for analysis, and the fluids may otherwise be analyzed. The gas and fluid analysis may be used to determine characteristics about the formation.

DETAILED DESCRIPTION

Certain aspects and examples of the present disclosure relate to predicted bias correction for a gas extractor and fluid sampling system. Bias can be a measure of how far an analytical result generated with a particular method diverges from an actual value. Various examples can include gas analysis of drilling fluid prior to a commencement of drilling operations. Various examples of the present disclosure may provide bias correction for a gas extraction and analysis system while drilling operations are ongoing. Such correction can produce composition results from gas analysis that more accurately represent reservoir compositions for methane through pentane. Bias corrections can be made in real-time at a wellbore site.

Prior to drilling, a drilling fluid sample can be obtained and positioned in an extraction vessel. The drilling fluid sample can represent a drilling fluid that can be used during a drilling operation. The drilling fluid sample can be saturated with hydrocarbon gas generating a flushed drilling fluid sample. The hydrocarbon gas can, for example, include methane, ethane, propane, iso-butane, iso-pentane, n-pentane, or any suitable combination of the foregoing. With modifications, the hydrocarbon gas can also include ethylene and propylene. The hydrocarbon gas can include at least one determined concentration of at least one chemical species.

The flushed drilling fluid sample can be exposed to conditions (e.g. temperature, pressure, etc.) that the drilling fluid experiences during the gas extraction process. While exposed to these conditions, the extraction vessel can be connected to a gas chromatograph or similar equipment. A concentration per time can be plotted and a curve area per time can be determined for at least one chemical species of interest. A response curve can be fitted to the area per time. The response curve can be used to correct a bias in readings of formational gas readings while drilling.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

Figure 1:
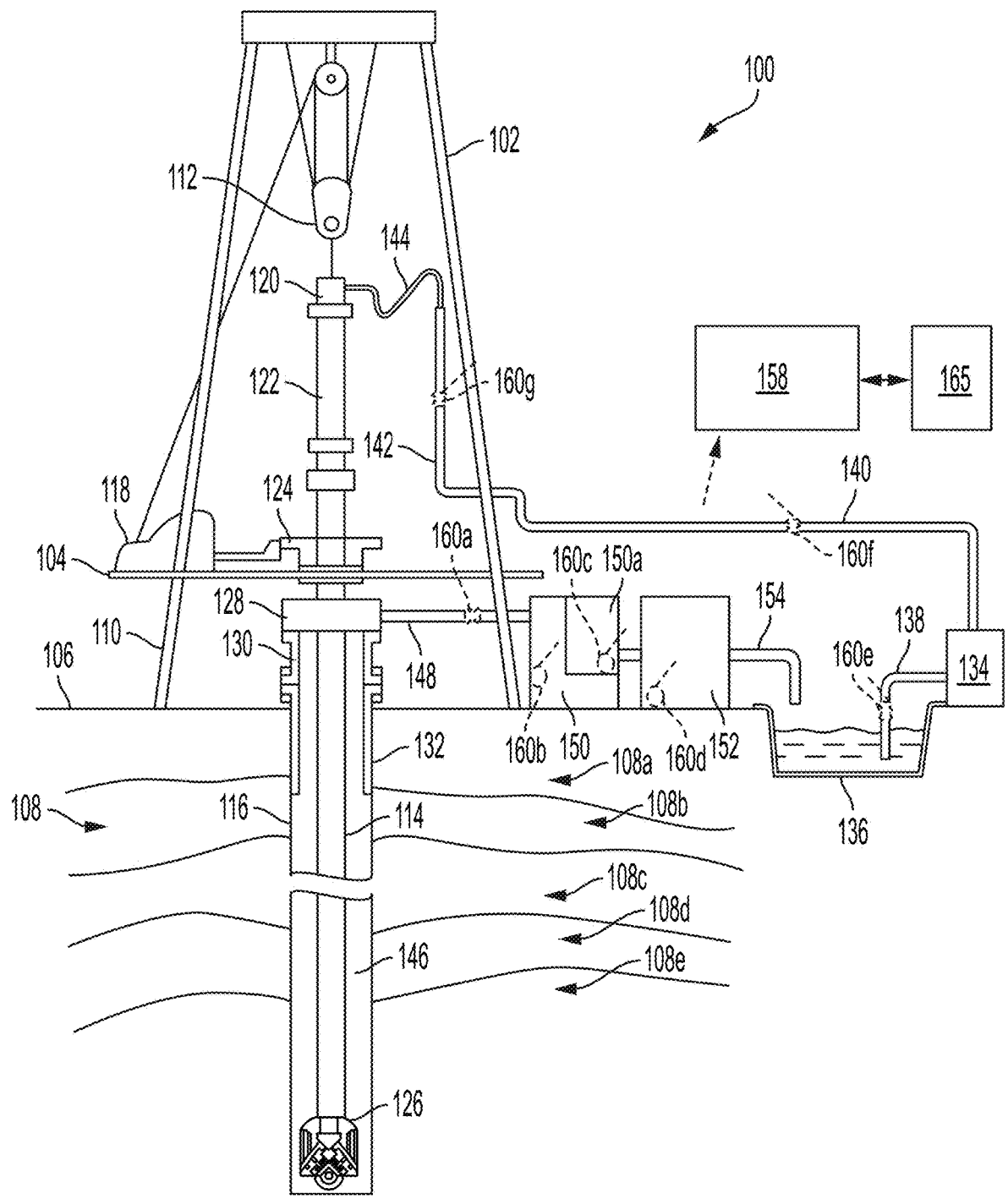
FIG. 1 is an example drilling system, according to one example of the present disclosure.

FIG. 1 is an example drilling system 100, according to one example of the present disclosure. The drilling system 100 may include a derrick 102 mounted on a floor 104 that is in contact with a surface 106 of a formation 108 through supports 110. The formation 108 may include a plurality of rock strata 108a-e, each of which may be made of different rock types with different characteristics. At least some of the strata may be porous and contain trapped fluids including liquid and gaseous components. Although the drilling system 100 includes an "on-shore" drilling system in which a floor 104 is at or near the surface 106, similar "off-shore" drilling systems are also possible and may be characterized by the floor 104 being separated from the surface 106 by a volume of water.

The derrick 102 may include a traveling block 112 for raising or lowering a drill string 114 disposed within a wellbore 116 in the formation 108. A motor 118 may control the position of the traveling block 112 and, therefore, the drill string 114. A swivel 120 may be coupled between the traveling block 112 and a kelly 122, which supports the drill string 114 as it is lowered through a rotary table 124. A drill bit 126 may be coupled to the drill string 114 and driven by a downhole motor (not shown) or rotation of the drill string 114 by the rotary table 124. As the drill bit 126 rotates, it creates the wellbore 116, which passes through one or more rock strata or layers of the formation 108.

The drill string 114 may extend into the wellbore 116 through a bell nipple 128, blowout preventer (BOP) 130, and wellhead 132. The wellhead 132 may include a portion that extends into the wellbore 116. In certain examples of the present disclosure, the wellhead 132 may be secured within the wellbore 116 using cement. The BOP 130 may be coupled to the wellhead 132 and the bell nipple 128, and the BOP 130 may work with the bell nipple 128 to prevent excess pressures from the formation 108 and wellbore 116 from being released at the surface 106. For example, the BOP 130 may include a ram-type BOP that closes an annulus 146 between the drill string 114 and the wellbore 116 in case of a blowout.

During drilling operations, drilling fluid, such as drilling mud, may be pumped into and received from the wellbore 116. In certain examples of the present disclosure, this drilling fluid may be pumped and received by a fluid circulation system that includes components on and below the surface 106. The fluid circulation system can include fluid containment components, flow actuator components, fluid treatment components and fluid flow conduits through which drilling fluid flows. In the example of the present disclosure shown, the fluid circulation system may include the fluid circulation, processing, and control elements between the bell nipple 128 and the swivel 120, as will be described below. Specifically, the fluid circulation system may include a mud pump 134 that pumps drilling fluid from a reservoir 136 through a suction line 138 into the drill string 114 at the swivel 120 through one or more fluid conduits, including pipe 140, stand-pipe 142, and hose 144. Once introduced at the swivel 120, the drilling fluid then may flow through the drill string 114, exiting at the drill bit 126 and returning through the annulus 146 between the drill string 114 and the wellbore 116 in an open-hole example, or between the drill string 114 and a casing (not shown) in a cased wellbore example. While in the wellbore 116, the drilling fluid may capture liquids and gases from the formation 108 as well as particulates or cuttings that are generated by the drill bit 126 engaging with the formation.

In certain examples of the present disclosure, the fluid circulation system further may include a return line 148 coupled to the bell nipple 128. Drilling fluid may flow through the return line 148 as it exits the annulus 146 via the bell nipple 128. The fluid circulation system may further include one or more fluid treatment mechanisms coupled to the return line 148 that may separate the particulates from the returning drilling fluid before returning the drilling mud to the reservoir 136, where it can be recirculated through the drilling system 100. In the example of the present disclosure shown, the fluid treatment mechanisms may include a mud tank 150 (which may also be referred to as a header box or possum belly) and a shale shaker 152. The mud tank 150 may receive the flow of drilling fluid from the annulus 146 and slow it so that the drilling fluid does not flow past the shale shaker 152. The mud tank 150 may also allow for cuttings to settle and gases to be released. In certain examples of the present disclosure, the mud tank 150 may include a trap box 150a (sometimes referred to as gumbo trap), which captures heavy clay particulates before the drilling fluid moves to the shale shaker 152, which may separate fine particulates from the drilling fluid using screens. The drilling fluid may flow from the fluid treatment mechanisms into the reservoir 136 through a fluid conduit 154.

According to aspects of the present disclosure, the drilling system 100 may further include a fluid analyzer 158 that can receive a drilling fluid sample. In some examples of the present disclosure, the drilling fluid sample can be received by the fluid analyzer 158 prior to a commencement of a drilling operation. The drilling fluid sample can represent a drilling fluid that can be used during the drilling operation. The drilling fluid sample can be a flushed drilling fluid sample that has been flushed with a hydrocarbon blend. The fluid analyzer 158 can analyze the liquid portions of the flushed drilling fluid sample, and the fluid analyzer 158 can extract and analyze gases within the flushed drilling fluid sample, which can, in turn, be used to determine bias in the fluid analyzer 158.

In some examples of the present disclosure, the drilling fluid sample can be received from the fluid circulation system. The fluid analyzer 158 may include a stand-alone machine or mechanism or may include integrated functionality of a larger analysis/extraction mechanism. The fluid analyzer 158 may be in fluid communication with and receive drilling fluid samples from access points within the fluid circulation system, including but not limited to, access point 160a on the return line 148, access point 160b on the mud tank 150, access point 160c on the trap box 150a, access point 160d on the shale shaker 152, access point 160e on the suction line 138, access point 160f on the pipe 140, and access point 160g on the stand-pipe 142. Fluid communication may be provided via at least one probe in fluid communication with the flow of drilling fluid at any one of the access points. In other examples of the present disclosure, the fluid analyzer 158 may be coupled to one or more of the fluid channels such that the flow of drilling fluid passes through the fluid analyzer 158.

At least some of the strata 108a-e may contain trapped liquids and gases that are held under pressure. As the wellbore 116 penetrates new strata, some of these fluids may be released into the wellbore 116. The released fluids may become suspended or dissolved in the drilling fluid as it exits the drill bit 126 and travels through the annulus 146. Each released liquid and gas may be characterized by its chemical composition, and certain formation strata may be identified by the liquids and gases it contains. As will be described below, the fluid analyzer 158 may take periodic or continuous samples of the drilling fluid, for example, by pumping, gravity drain or diversion of flow, or other means. The fluid analyzer 158 may generate gas from the fluid sample that may be used to determine the chemical composition of the drilling fluid. This chemical composition may be used to determine the types of liquids and gases that are suspended within the drilling fluid, which can then be used to determine a formation characteristic of the formation 108. In some examples, determination of formation characteristics can be performed in real-time.

The fluid analyzer 158 may include or be communicably coupled to a computing device 165. In the example of the present disclosure shown, the computing device 165 may include a computing system located at the surface that may receive measurements from the fluid analyzer 158 and process the measurements to determine at least one formation characteristic based on the drilling fluid sample. For example, the computing device 165 may include a processor that can execute program code stored on a machine-readable medium.

In certain examples of the present disclosure, the computing device 165 may further control the operation of the fluid analyzer 158, including how often the fluid analyzer 158 takes measurements and fluid samples. In certain examples of the present disclosure, the computing device 165 may be integrated with the fluid analyzer 158. In other examples of the present disclosure, the computing device 165 may be a distinct system that receives measurements from a variety of devices in the drilling system 100 or controls the operation of other devices.

The output of the fluid analyzer 158 may include electrical signals or electrically encoded data that corresponds to measurements taken by the fluid analyzer 158 of liquids or extracted gases from the flushed drilling fluid samples. In certain embodiments, the computing device 165 may receive output from the fluid analyzer 158 and determine characteristics of the liquid or extracted gas from the flushed drilling fluid sample, such as corresponding chemical compositions of liquid or gaseous components. The chemical compositions of the flushed drilling fluid sample may include the types of chemicals found in the hydrocarbon blend and their relative concentrations. The computing device 165 may determine the chemical composition and bias caused by a gas extraction and sampling system in the fluid analyzer 158, for example, by receiving an output from the fluid analyzer 158, and comparing the output to a first data set corresponding to known chemical compositions. The computing device 165 can apply a correction to the bias caused by the gas extraction and sampling system.

In certain examples of the present application, the computing device 165 may fully characterize a chemical composition of a drilling fluid sample that can be received during a drilling operation. Characterization of the chemical composition of the drilling fluid sample may be more accurate due to applying the correction to the bias caused by the gas extraction and sampling system. The chemical composition characterization of the drilling fluid sample may be based on the output from the fluid analyzer 158. The computing device 165 may further determine the types of liquids and gases suspended within the drilling fluid sample based on the determined chemical composition. Additionally, in certain embodiments, the computing device 165 may determine a characteristic formation using the determined types and concentrations of liquids and gases suspended within the drilling fluid. The computing device 165 may determine formation characteristics by comparing the determined types and concentrations of liquids and gases suspended within the drilling fluid sample to a second data set that includes types and concentrations of liquids and gases suspended within the drilling fluid of known subterranean formations.

The computing device 165 may determine a formation characteristic using the determined chemical composition. An example determined chemical composition for the liquid portion of a drilling fluid may be 15% chemical/compound A, 20% chemical/compound B, 60% chemical/compound C, and 5% other chemicals/compounds. Example wellbore characteristics may include, but are not limited to, the type of rock in the formation 108, the presences of hydrocarbons in the formation 108, the production potential for one or more of strata 108*a-e*, and the movement of fluid within one or more of strata 108*a-e*. In certain examples of the present disclosure, the computing device 165 may determine the formation characteristic using the determined chemical composition characteristics by comparing the determined chemical composition to a second data set that includes chemical compositions of known subterranean formations. For example, the determined chemical composition may correspond to a drilling fluid with suspended fluid from a shale layer in the formation 108.

Figure 2:
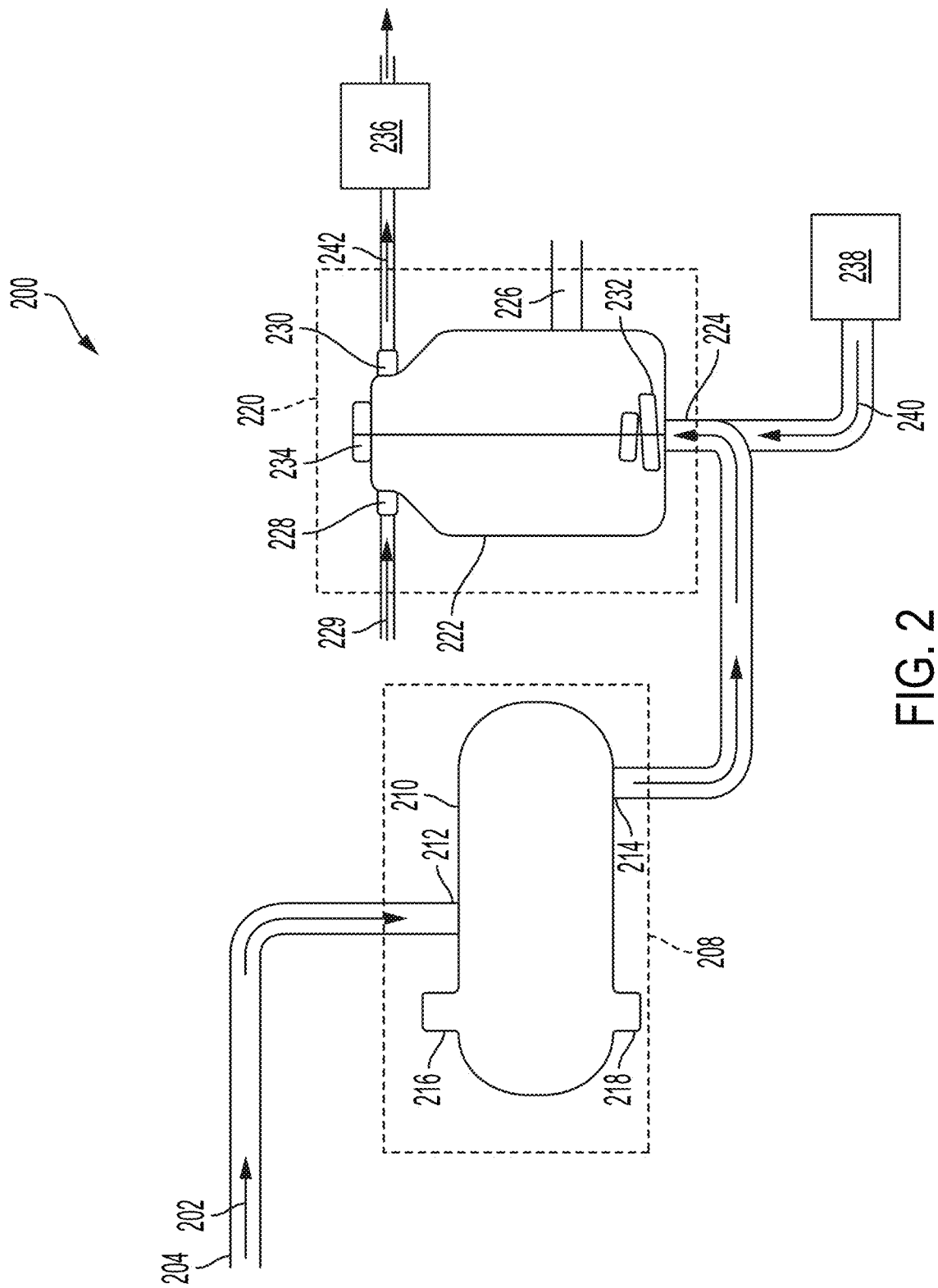
FIG. 2 is a block diagram of an example gas extractor system that extracts gases from flushed drilling fluid samples, according to one example of the present disclosure.

FIG. 2 is a diagram of an example gas extraction system 200 that extracts gases from a drilling fluid sample 202, according to some examples of the present disclosure. In some examples, the drilling fluid sample 202 can be received prior to the commencement of drilling operations. The drilling fluid sample 202 can represent a drilling fluid that will be used in a drilling operation. One or more of the components of gas extraction system 200 may be implemented by a fluid analyzer 158. In the example of the present disclosure shown, the gas extraction system 200 may receive the drilling fluid sample 202 through a fluid conduit or pipe 204 that leads the drilling fluid sample 202 toward a sample-temperature controller 208 of the gas extraction system 200. The sample-temperature controller 208 may alter or maintain the temperature of the drilling fluid sample 202 at a set temperature, which may be hotter, cooler, or the same as the temperature of the drilling fluid sample 202 as it enters the gas extraction system 200. In the examples of the present disclosure shown, the sample-temperature controller 208 includes a shell and tube heat exchanger with two sets of fluid inlets and outlets: a first inlet 212 and first outlet 214, and a second inlet 216 and second outlet 218. Each set of fluid inlets and outlets may correspond to a different segregated fluid pathway through the shell 210. For example, the second inlet 216 and second outlet 218 may correspond to a fluid pathway including a system of sealed tubes (not shown) located within the shell 210, and the first inlet 212 and first outlet 214 may correspond to a fluid pathway in which fluid flows around the system of sealed tubes. The system of sealed tubes may include u-tubes, single-pass straight tubes, double-pass straight tubes, or other types of sealed tubes.

In certain examples of the present disclosure, the drilling fluid sample 202 may enter the shell 210 through the first inlet 212 and exit through the first outlet 214. A second fluid or gas may enter the shell 210 through the second inlet 216 and exit through the second outlet 218. Either the second fluid or the drilling fluid sample 202 may flow through the system of sealed tubes. The second fluid may be at or near a set temperature for the drilling fluid sample 202 and energy transfer may occur between the drilling fluid sample 202 and the second fluid through the tubes until the drilling fluid sample 202 has reached the set temperature. The tubes may conduct thermal energy. Notably, although a shell and tube heat exchanger are described herein, the sample-temperature controller 208 may include other types of heat exchangers, including, but not limited to, thermoelectric, electric, and finned tube heat exchangers that are driven by electricity, gas, or liquid; u-tube heat exchangers; etc.

Once at or near the set temperature, the drilling fluid sample 202 may be received at a gas extractor 220 of the gas extraction system 200, the gas extractor 220 being in fluid communication with the sample-temperature controller 208. Example gas extractors include, but are not limited to, continuously stirred vessels, distillation columns, flash columns, separator columns, bench-scale extraction vessels, constant volume/constant temperature (CVCT) gas extractors, or any other vessel that allows for the separation and expansion of gas from liquids and solids. In the example of the present disclosure shown, the gas extractor 220 can include a vessel 222 that receives the drilling fluid sample 202 through a fluid inlet 224. The vessel 222 can be in fluid communication with a gas reservoir 238, which can contain a hydrocarbon blend 240. The hydrocarbon blend 240 may pass through the fluid inlet 224 of the vessel 222 to flush the drilling fluid sample 202. The vessel can further include a fluid outlet 226 through which a portion of a flushed drilling fluid sample 242 will flow after a gas extraction process. The gas extractor 220 may further include an impeller 232 within the vessel 222 to agitate the drilling fluid sample 202 as it enters the vessel 222 or while it is being flushed with the hydrocarbon blend 240. The impeller 232 may be driven by a motor 234 that rotates the impeller 232 to create a turbulent flow of the flushed drilling fluid sample 242 within the vessel 222, which causes gases trapped within the solids and liquids of the flushed drilling fluid sample 242 to be released into the vessel 222. Although an impeller 232 is shown, it is possible to use other types of agitators.

Gases within the vessel 222 that are released from the flushed drilling fluid sample 242 through the agitation process may be removed from the vessel 222 through a gas outlet 230. In certain examples of the present disclosure, the vessel 222 may include a gas inlet 228, and at least one carrier gas 229 may be introduced into the vessel 222 through the gas inlet 228. The at least one carrier gas 229 may include atmospheric or purified gases that are introduced into the vessel 222 to aide in the movement of the extracted gases to a gas outlet 230. The at least one carrier gas 229 may have known chemical compositions such that their presence can be accounted for when the extracted gases from the gas outlet 230 are analyzed.

Although in some examples of the present disclosure, the sample-temperature controller 208 and gas extractor 220 are shown as separate devices, it may be possible to combine the functionality into a single device. For example, heat exchange may be accomplished through the vessel 222, bringing the drilling fluid sample 202 or the flushed drilling fluid sample 242 to a set temperature while it is in the vessel 222. In other examples of the present disclosure, the sample-temperature controller 208 may be optional, and the drilling fluid sample 202 may be directed to the gas extractor 220 without flowing through a sample-temperature controller 208. In certain examples of the present disclosure, the gas outlet 230 of the gas extractor 220 may be coupled to a pump 236 which may deliver an extracted gas sample out from the gas extractor 220.

Figure 3:
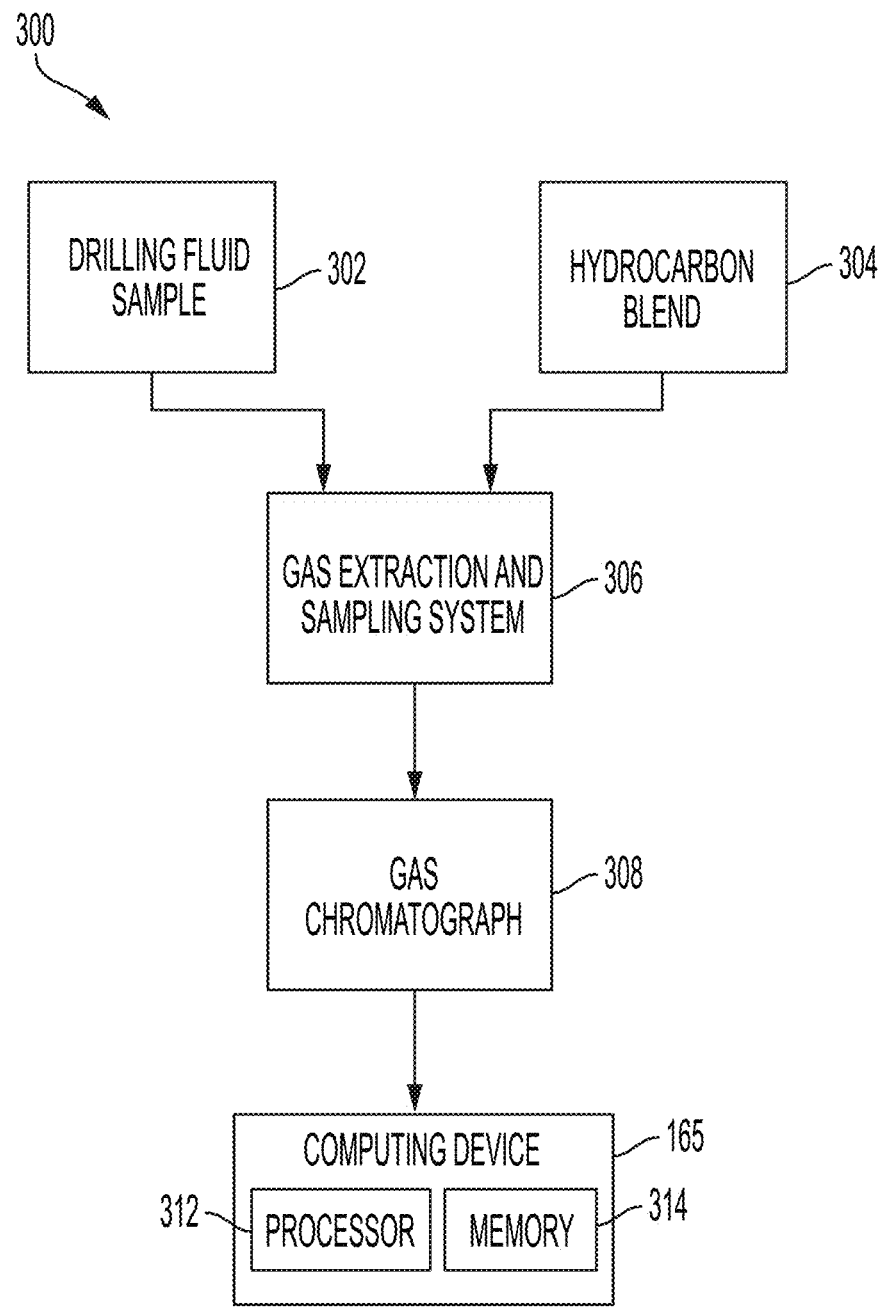
FIG. 3 is a block diagram depicting an example system for drilling fluid sampling and gas extraction and analysis, according to one example of the present disclosure.

FIG. 3 depicts a block diagram of an example system 300 for drilling fluid sampling and gas extraction and analysis, according to some examples of the present disclosure. The system 300 can include a drilling fluid sample 302, a hydrocarbon blend 304, a gas extraction and sampling system 306, a gas chromatograph 308, and a computing device 165. An example of the system 300 is the gas extraction system 200 illustrated in FIG. 2. The drilling fluid sample 302 and hydrocarbon blend 304 can be input into the gas extraction and sampling system 306. The hydrocarbon blend can be a gaseous mixture that can include a mixture of one or more of methane, ethane, propane, iso-butane, n-butane, iso-pentane, n-pentane, ethylene, and propylene in known quantities. For example, the drilling fluid sample 302 can be flushed by the hydrocarbon blend 304 generating a flushed drilling fluid sample. An output of the gas extraction and sampling system 306, such as the gas output from gas outlet 230 in FIG. 2, can be coupled to an input of the gas chromatograph 308. The gas chromatograph can measure or otherwise determine concentrations of species based on the extracted gas received from the gas extraction and sampling system 306. Storage of the flushed drilling fluid sample in a vessel can minimize dissolved formational gas loss.

In some examples of the present disclosure, the gas chromatograph 308 can determine species of the flushed drilling fluid sample that can include methane, ethane, propane, iso-butane, n-butane, iso-pentane, and n-pentane. In some examples of the present disclosure, the gas chromatograph 308 can be modified to also determine ethylene and propylene. The computing device 165 can be communicatively coupled to the gas chromatograph 308 to receive values of the concentration of each species of the extracted gas over time from the gas chromatograph 308. The computing device 165 can perform, by any combination of hardware, software, firmware, etc., the operations described herein. For example, the device 310 can include a processor 312 that executes program code stored in a memory 314 also included in the computing device 165. As further described below, the computing device 165 can plot concentrations of each species versus time. The computing device 165 can also generate an area per concentration curve for each chemical species. The computing device 165 can fit the area per concentration curve with a response curve for each chemical species. The computing device 165 can also apply the response curve to original values of concentration of each species to create corrected values of concentration of each species to correct for system bias.

Figure 4A:
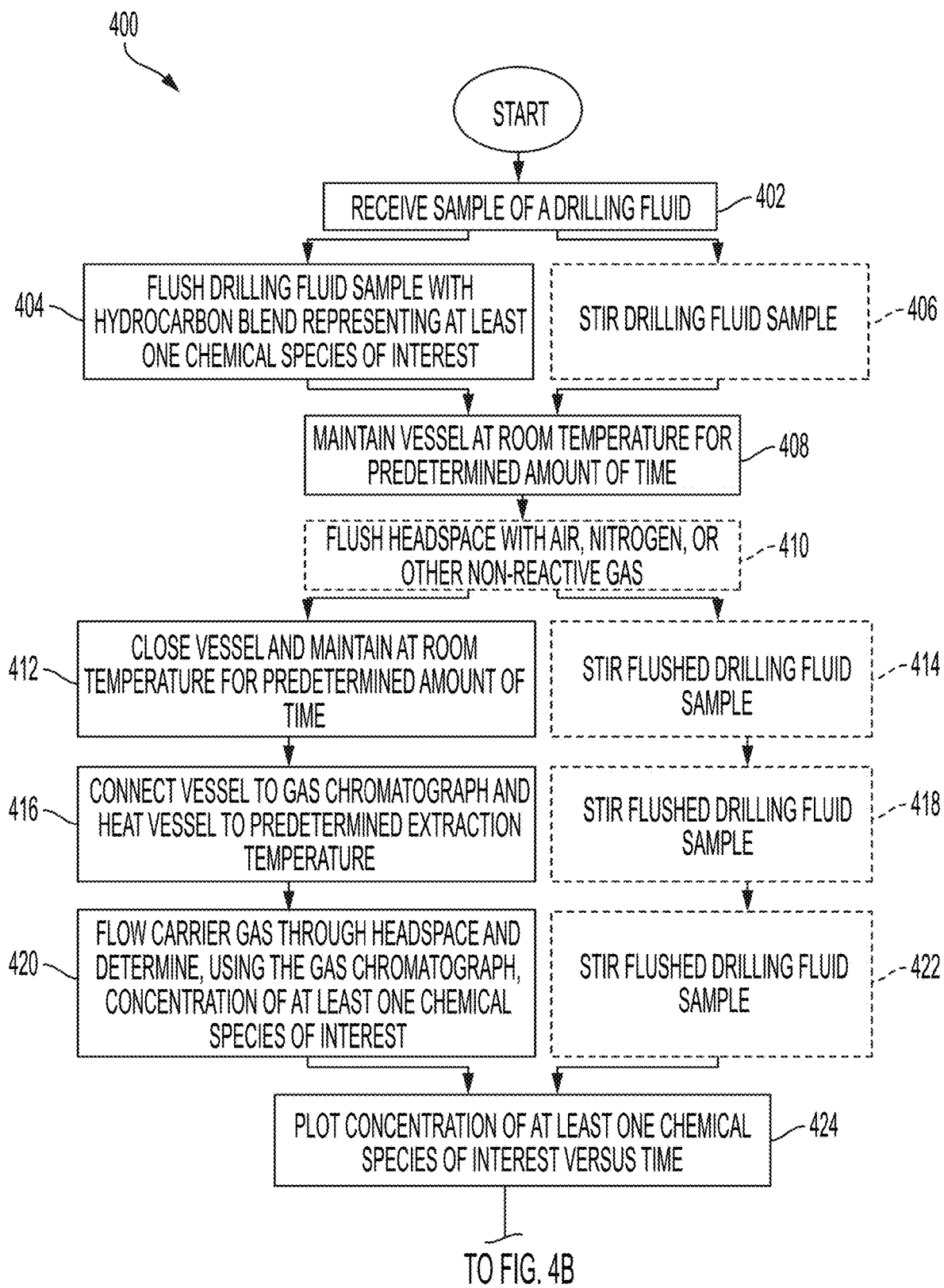
FIGS. 4A and 4B illustrate a flowchart depicting a process for drilling fluid sampling and gas extraction and analysis, according to one example of the present disclosure.
Figure 4B:
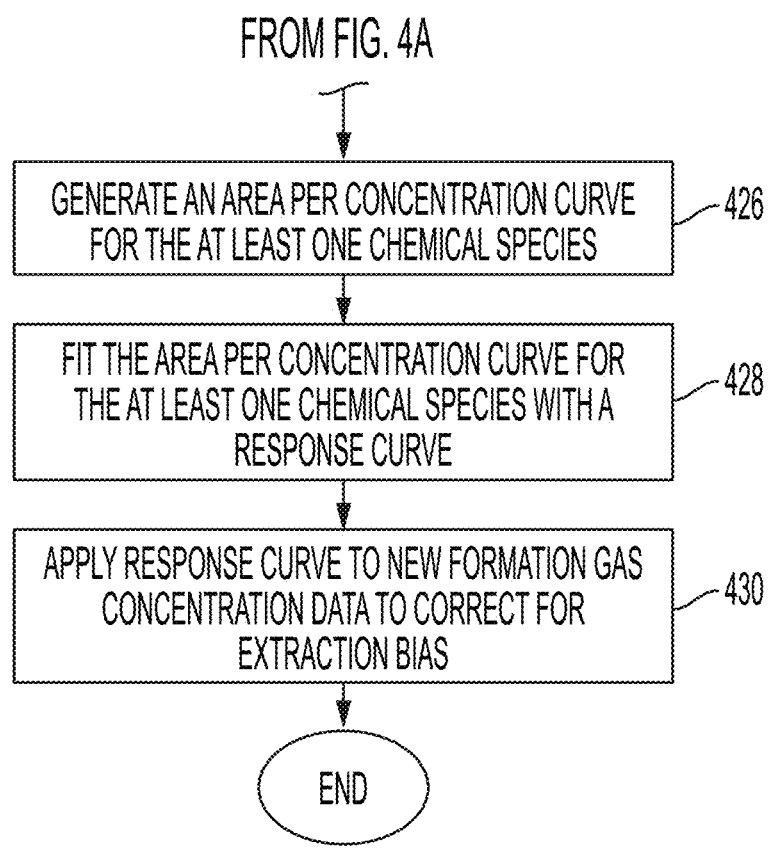

FIGS. 4A and 4B illustrate a flowchart of a process 400 for drilling fluid sampling and gas extraction and analysis, according to some examples of the present disclosure. The process 400 may be performed by software, firmware, hardware or a combination thereof. At block 402, the process 400 involves providing a drilling fluid sample to a vessel. The drilling fluid sample can be small (e.g. contained in a bench-scale extraction vessel) or large (contained in a 20 liter extraction vessel). The drilling fluid sample can represent a drilling fluid that will be used during a drilling operation such as depicted and described with respect to the drilling system 100 of FIG. 1. In some examples of the present disclosure, the bench-scale extraction vessel is a 1 liter extraction vessel. In some examples of the present disclosure, the vessel can have a maintained headspace.

At block 404, the process 400 involves flushing the drilling fluid sample with a hydrocarbon blend representing at least one chemical species of interest. A flushed drilling fluid sample can be generated. In some examples, the drilling fluid sample can be flushed by bubbling the hydrocarbon blend through the base of the vessel into the drilling fluid sample. The hydrocarbon blend can include methane, ethane, propane, iso-butane, n-butane, iso-pentane, n-pentane, ethylene, propylene, or any suitable combination of the foregoing.

At block 406, the process 400 involves stirring the drilling fluid sample while flushing the drilling fluid sample with a hydrocarbon blend. The drilling fluid sample can be stirred by an impeller 232. Stirring the drilling fluid sample at block 406 can occur at the same time that the drilling fluid sample is flushed with a hydrocarbon blend at block 404. In some examples, stirring the drilling fluid sample at block 406 may be optional.

At block 408, the process 400 involves maintaining the vessel at room temperature for a predetermined amount of time. In some examples of the present disclosure, the predetermined amount of time is at least thirty minutes. In additional examples, the predetermined amount of time can be at least one hour.

At block 410, process 400 involves flushing the headspace with air, nitrogen or another non-reactive gas. Flushing the headspace can remove reactive gases whose presence can affect accuracy of measurements. In some examples of the present disclosure, flushing the headspace may be optional.

At block 412, the process 400 involves closing the vessel and holding the vessel at room temperature for a predetermined amount of time. The vessel can be maintained at room temperature to allow the flushed drilling fluid sample to reach an equilibrium state. In some examples of the present disclosure, the predetermined amount of time can be at least thirty minutes.

At block 414, the process 400 involves stirring the flushed drilling fluid sample. Stirring the flushed drilling fluid sample at block 414 can be performed while holding the vessel at room temperature at block 412. In some examples, stirring the flushed drilling fluid sample at block 414 may be optional.

At block 416, the process 400 involves connecting the vessel to a gas chromatograph or similar type of equipment. The vessel can be heated to a predetermined extraction temperature. The gas chromatograph can perform a gas concentration measurement and other analyses. In some examples, the vessel can be connected to the gas chromatograph prior to receiving the drilling fluid sample.

At block 418, the process 400 involves stirring the flushed drilling fluid sample. Stirring the flushed drilling fluid sample at block 418 can occur while the vessel is heated at block 416. In some examples, stirring the flushed drilling fluid sample at block 418 may be optional.

At block 420, the process 400 involves flowing a carrier gas through the headspace of the vessel and the gas chromatograph determines a concentration of at least one chemical species of interest. The carrier gas aids the movement of extracted gas towards the gas chromatograph through a gas outlet. For example, with reference to FIG. 3, the gas chromatograph 308 determines concentration of each chemical species of the extracted dissolved gas over time received from the gas extraction and sampling system 306.

At block 422, the process 400 involves stirring the flushed drilling fluid sample. Stirring the flushed drilling fluid sample at block 422 can occur while the gas chromatograph determines the concentration of the at least one chemical species of interest at block 420. In some examples, stirring the flushed drilling fluid sample at block 422 may be optional.

At block 424, the process 400 involves plotting a concentration of each chemical species detected in the flushed drilling fluid sample versus time. For example, with reference to FIG. 3, the computing device 165 may receive the concentration of each chemical species from the gas chromatograph 308 and plot a concentration of each chemical species versus time. To illustrate, FIG. 6 depicts a graph 600 of propane concentration in parts per million (PPM) along the Y-axis and time in seconds along the X-axis.

At block 426, the process 400 involves generating an area per concentration curve for each chemical species. For example, with reference to FIG. 3, the computing device 165 can generate an area per concentration curve for each chemical species based on the concentration over time curves generated for each species such as the curve depicted in FIG. 6. In some examples of the present disclosure, a total concentration per time value can be generated from integrating the area under a concentration over time curve at each of a series of points in time. In this manner, the integration can generate area under the curve data by calculating an area under the curve for each time point. Results of an integration can be displayed using an area per concentration curve. The area per concentration curve can include total concentration per time point on the Y-axis and instantaneous concentration values directly measured for each time point on the X-axis.

Figure 6:
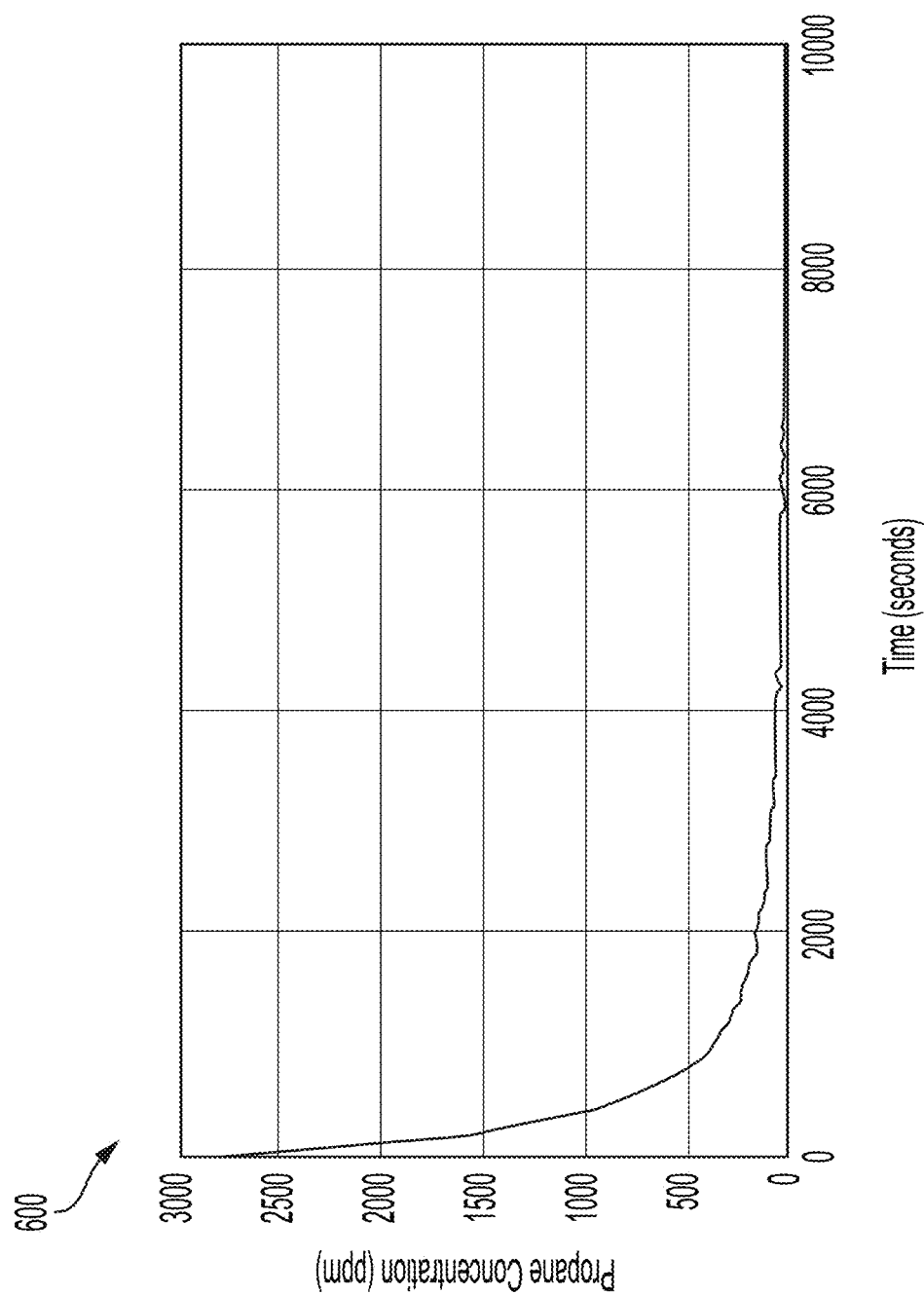
FIG. 6 is a graph depicting an example concentration over time, according to one example of the present disclosure.
Figure 7:
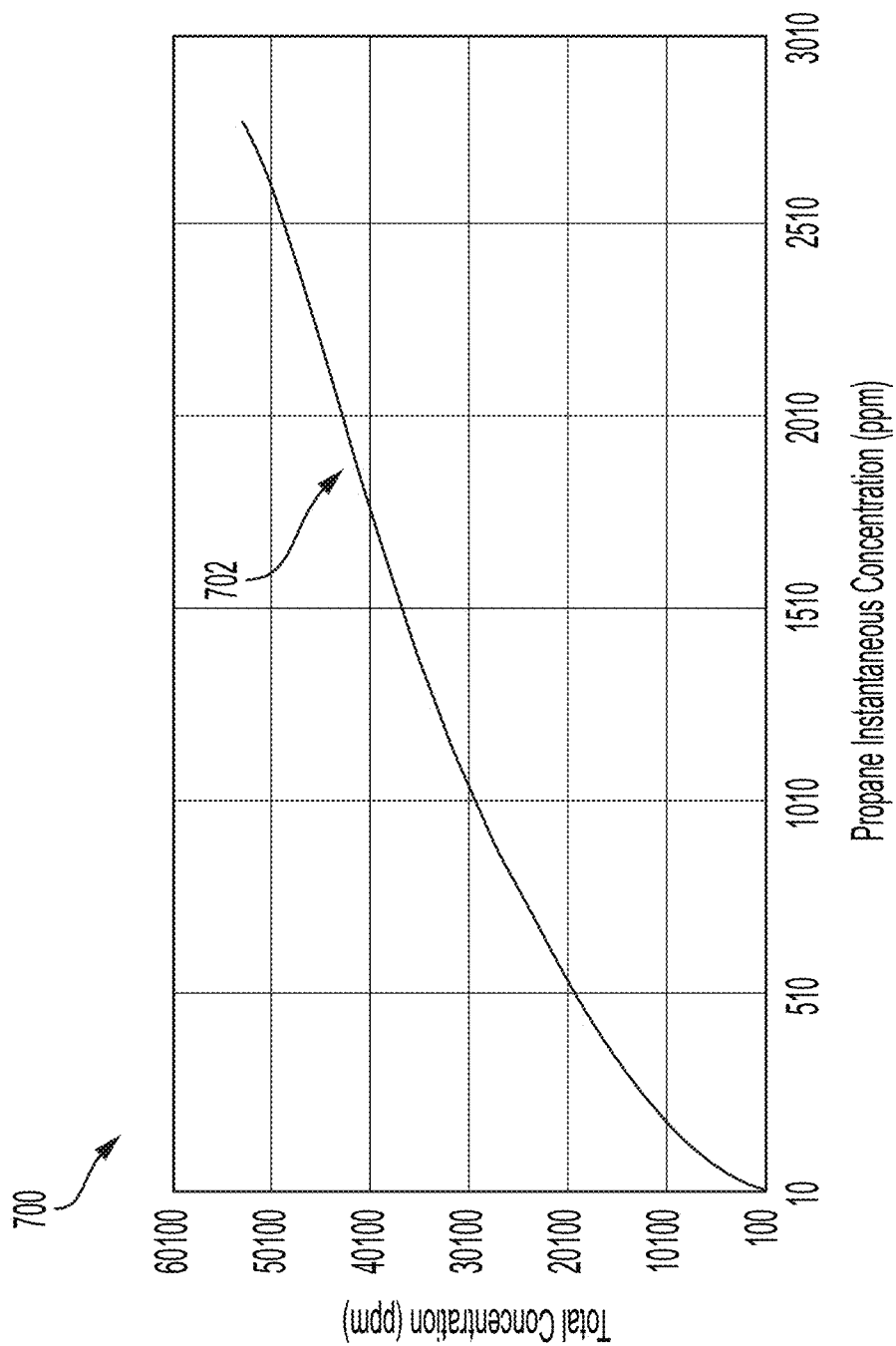
FIG. 7 is a graph depicting an area per concentration curve derived from the example concentration over time of FIG. 6, according to one example of the present disclosure.

To illustrate, FIG. 7 depicts a graph of an area per concentration curve derived from the example concentration over time of FIG. 6, according to some examples of the present disclosure. FIG. 7 depicts a graph 700 of total concentration per time point of propane in PPM along the Y-axis and propane instantaneous concentration in PPM along the X-axis. The graph 700 includes an area per concentration curve 702. In some examples of the present disclosure, a computing device 165 can generate the area per concentration curve 702 from a numerical integration of a concentration over time curve or from a direct integration of a fitted curve of the concentration over time curve.

Figure 8:
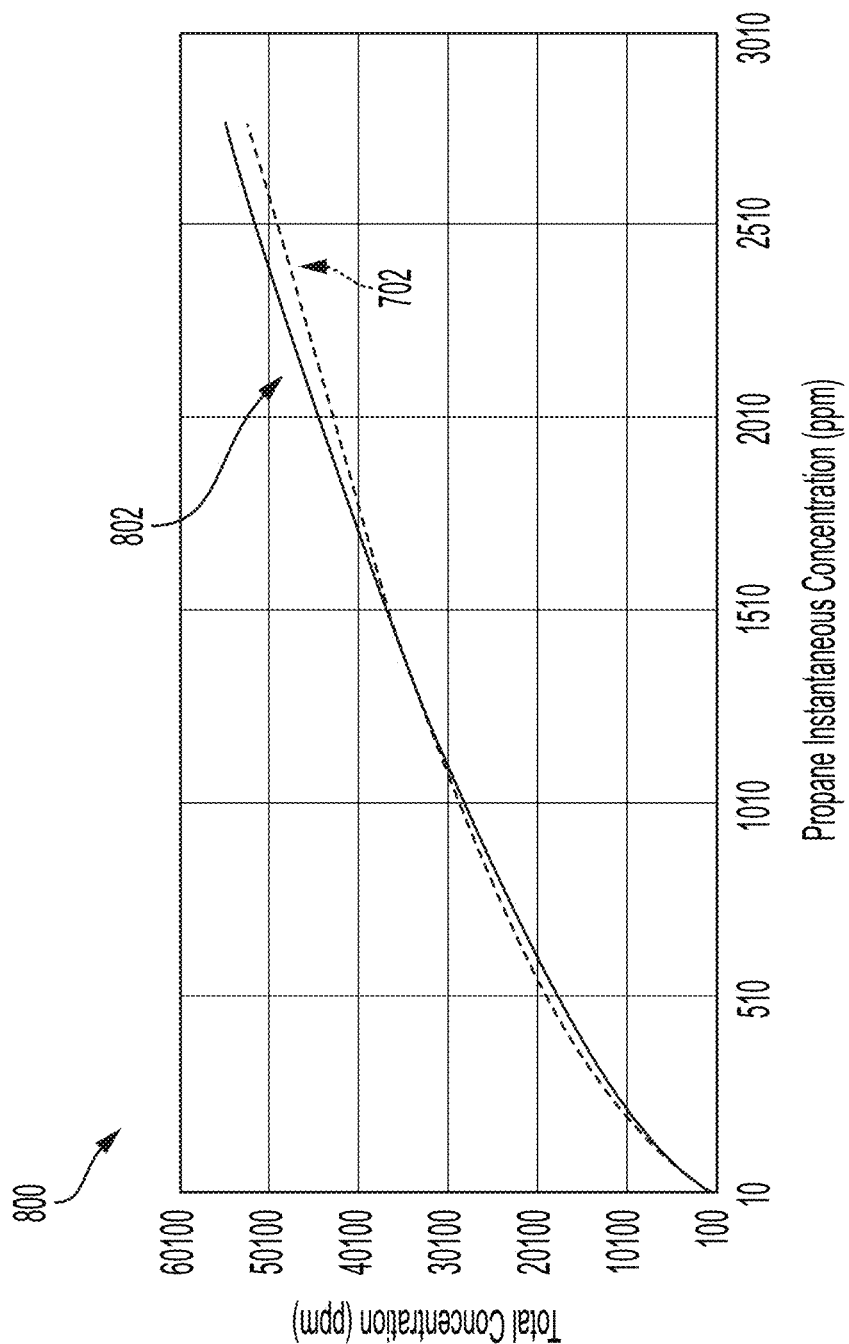
FIG. 8 is a graph depicting the area per concentration curve of FIG. 7 fitted with a response curve, according to one example of the present disclosure.

At block 428, the process 400 involves fitting the area per concentration curve for each chemical species with a response curve. For example, with reference to FIG. 3, the computing device 165 can fit the area per concentration with a response curve for each chemical species. To illustrate, FIG. 8 depicts a graph 800 of the area per concentration curve 702 of FIG. 7 fitted with a response curve 802, according to some examples of the present disclosure. The graph 800 presents total concentration of propane in PPM along the Y-axis and propane instantaneous concentration in PPM along the X-axis. The area per concentration curve 702 from the graph 700 is reproduced on the graph 800. The graph 800 also includes a fitted response curve 802. A best fitted curve can be selected. For example, the fitted curve can be power log, polynomial, logarithmic, exponential, etc.

Figure 9:
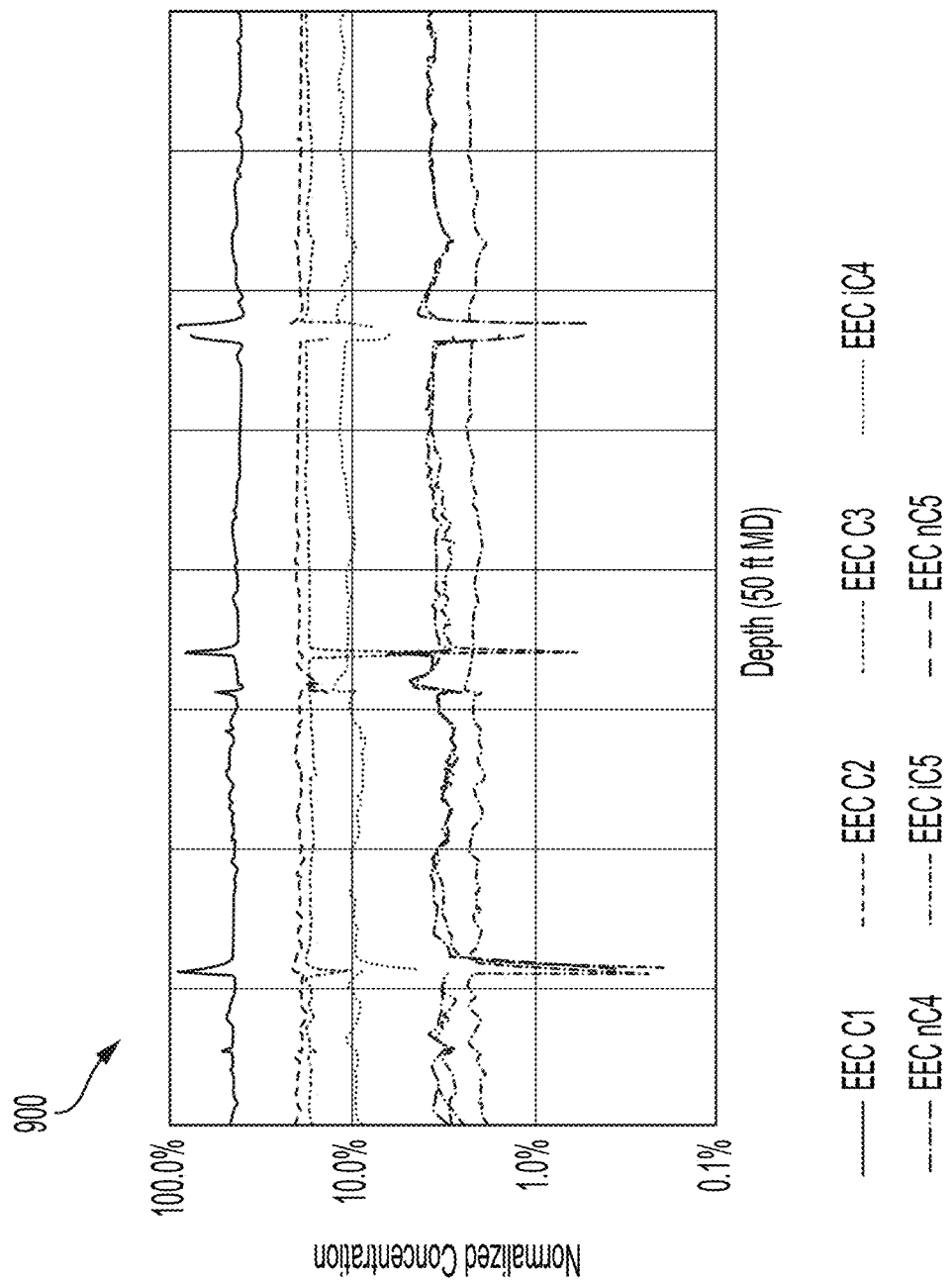
FIG. 9 is a graph depicting an example normalized correction of concentrations using the area under the response curve of FIG. 8, according to one example of the present disclosure.

At block 430, the process 400 involves applying response curves to original values of concentration of each chemical species to create corrected values of concentration of each chemical species to correct for system bias. For example, with reference to FIG. 3, the computing device 165 may apply the response curve to original values of concentration of each chemical species to create corrected values of concentration of each chemical species to correct for system bias. For example, the fitted curve can be represented as an equation in which a new value is defined as a function of a previously determined value. So, each point in time of the raw data can be adjusted based on the equation defined by the fitted curve. To illustrate, FIG. 9 depicts a graph of an example normalized correction of concentrations using the area under the response curve of FIG. 8, according to some examples of the present disclosure.

Figure 10:
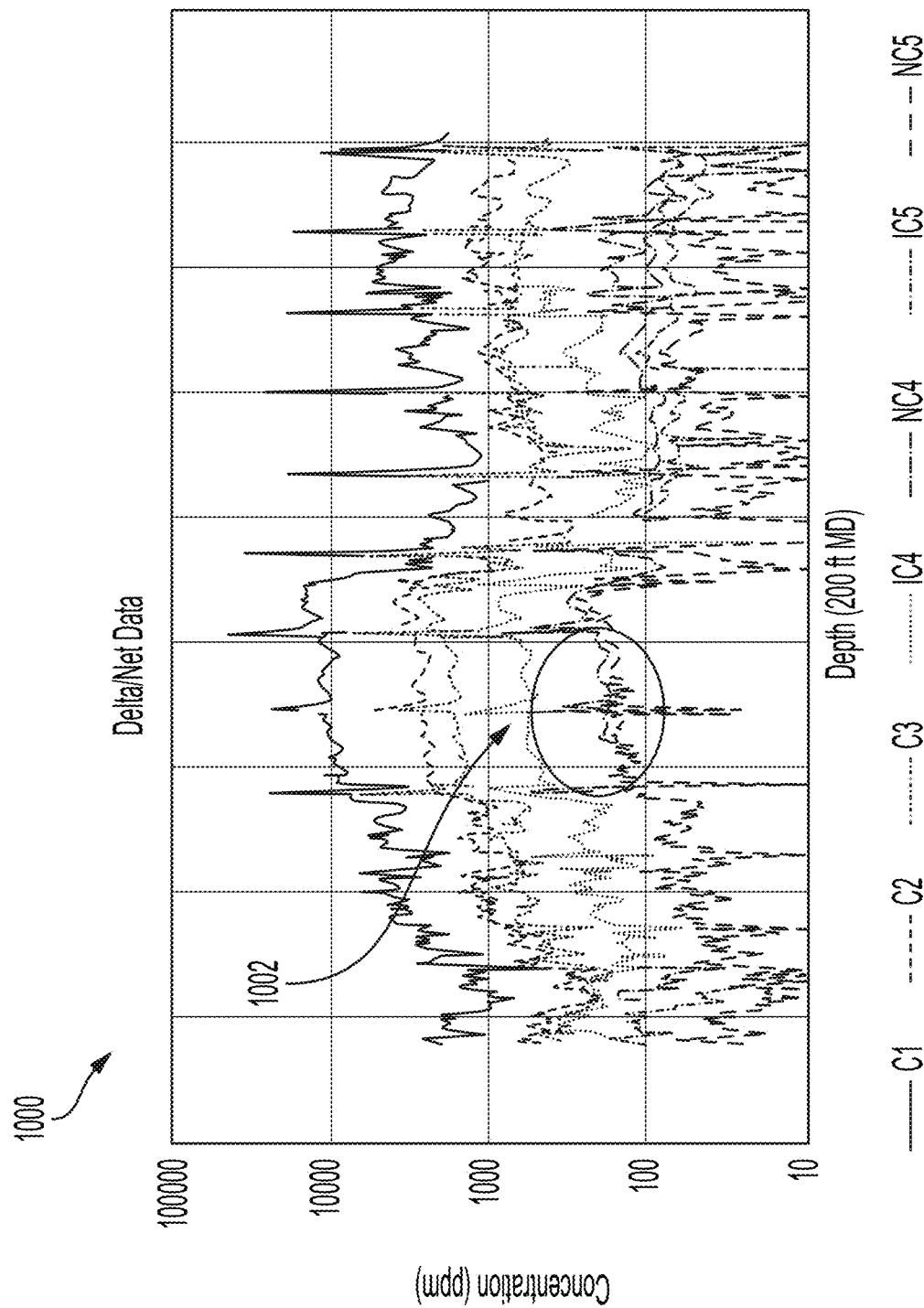
FIG. 10 is a graph depicting example concentrations over a depth of a wellbore without correction of system bias, according to one example of the present disclosure.
Figure 11:
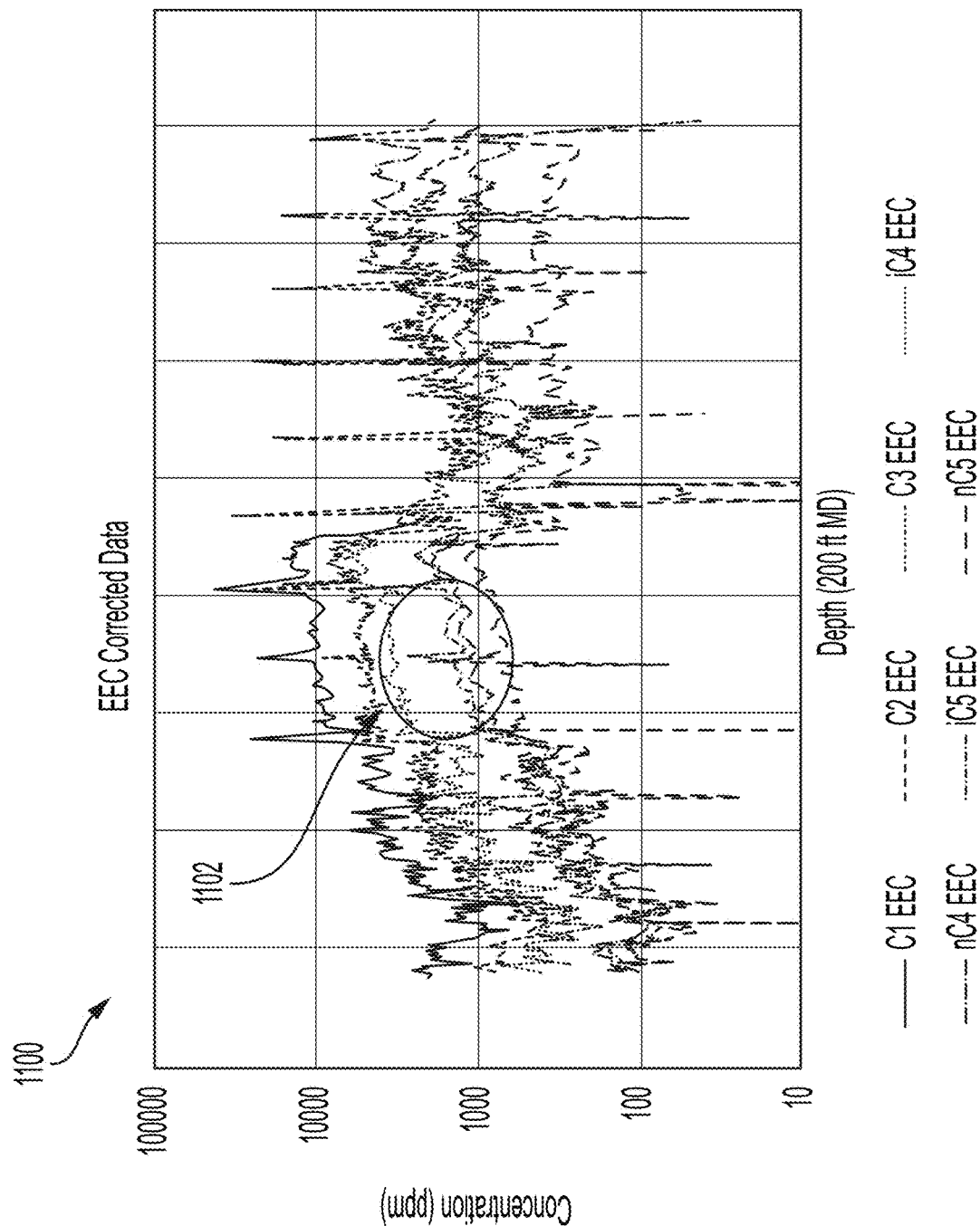
FIG. 11 is a graph depicting example concentrations over the depth of the wellbore of FIG. 10 with correction of system bias, according to one example of the present disclosure.

To further illustrate, FIG. 10 depicts a graph of example hydrocarbon concentrations in a drilling fluid sample over a depth of the wellbore without correction of system bias, according to some examples of the present disclosure. In particular, FIG. 10 depicts a graph 1000 of values of seven concentrations (C1, C2, C3, IC4, NC4, IC5, and NC5) in PPM over a range of depth. These values are prior to correction of system bias. For example, an area 1002 of the graph 1000 highlights the values of the concentration NC5 just greater than 100 PPM. FIG. 11 depicts a graph 1100 of the example concentrations over a depth of wellbore of FIG. 10 with correction of system bias, according to some examples of the present disclosure. An area 1102 of the graph 1100 corresponds to the area 1002 of the graph 1000. As shown, the values of the concentration NC5 can be found to be greater than 1000 PPM because of the adjustment for system bias.

In some examples of the present disclosure, a formation characteristic of the subterranean formation can be determined based on the corrected values of concentration of each chemical species. For example, the computing device 165 can determine a formation characteristic based on the corrected values of concentration of each chemical species found in a drilling fluid sample used during a drilling operation. Determining the formation characteristic using the determined chemical composition may include comparing the determined chemical composition to known chemical compositions of subterranean formations. The formation characteristics may include at least one of a type of rock in the subterranean formation, the presence of hydrocarbons in the subterranean formation, the production potential for a stratum of the subterranean formation, and the movement of fluid within the strata.

In some examples of the present disclosure, hydrocarbon recovery operations can be modified, while drilling operations are ongoing, based on the determined fluid formation characteristic of the subterranean formation. For example, if the determined fluid formation characteristic of the subterranean formation is essentially gas, the production operation can be set up for gas production. Conversely, if the determined fluid formation characteristic of the subterranean formation is essentially oil, the production operation can be set up for oil production. If the determined fluid formation characteristic of the subterranean formation is a combination of oil and gas, the production operation can be set up to produce oil and gas.

Thus, various examples of the present disclosure do not take into account parameters of the gas extraction and sampling system to correct for bias of the gas extraction and sampling system. Such examples provide for a simplified technique to correct the bias because the correction is independent the specifics of the system.

Figure 5A:
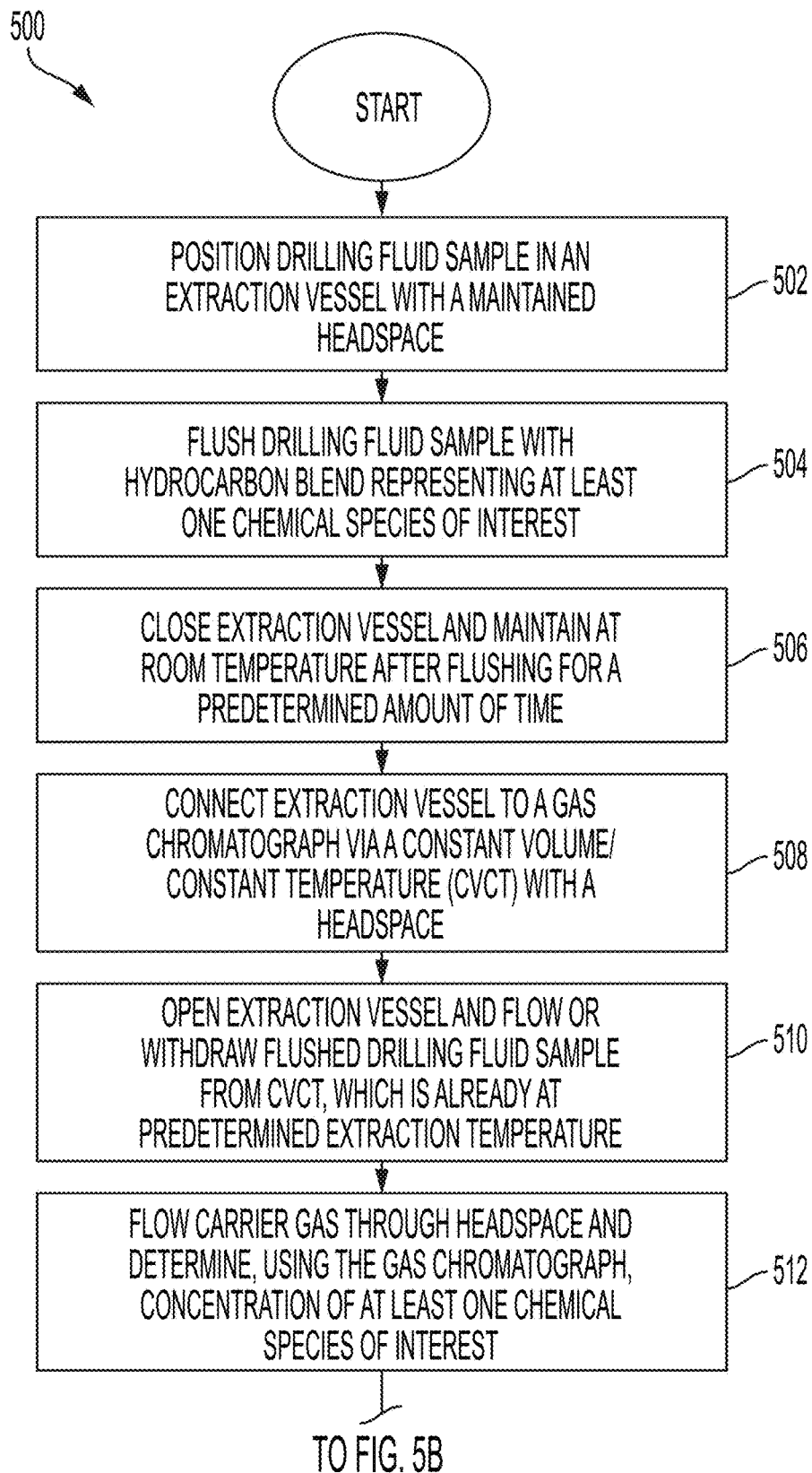
FIGS. 5A and 5B illustrate a flowchart depicting an additional process for drilling fluid sampling and gas extraction and analysis, according to one example of the present disclosure.
Figure 5B:
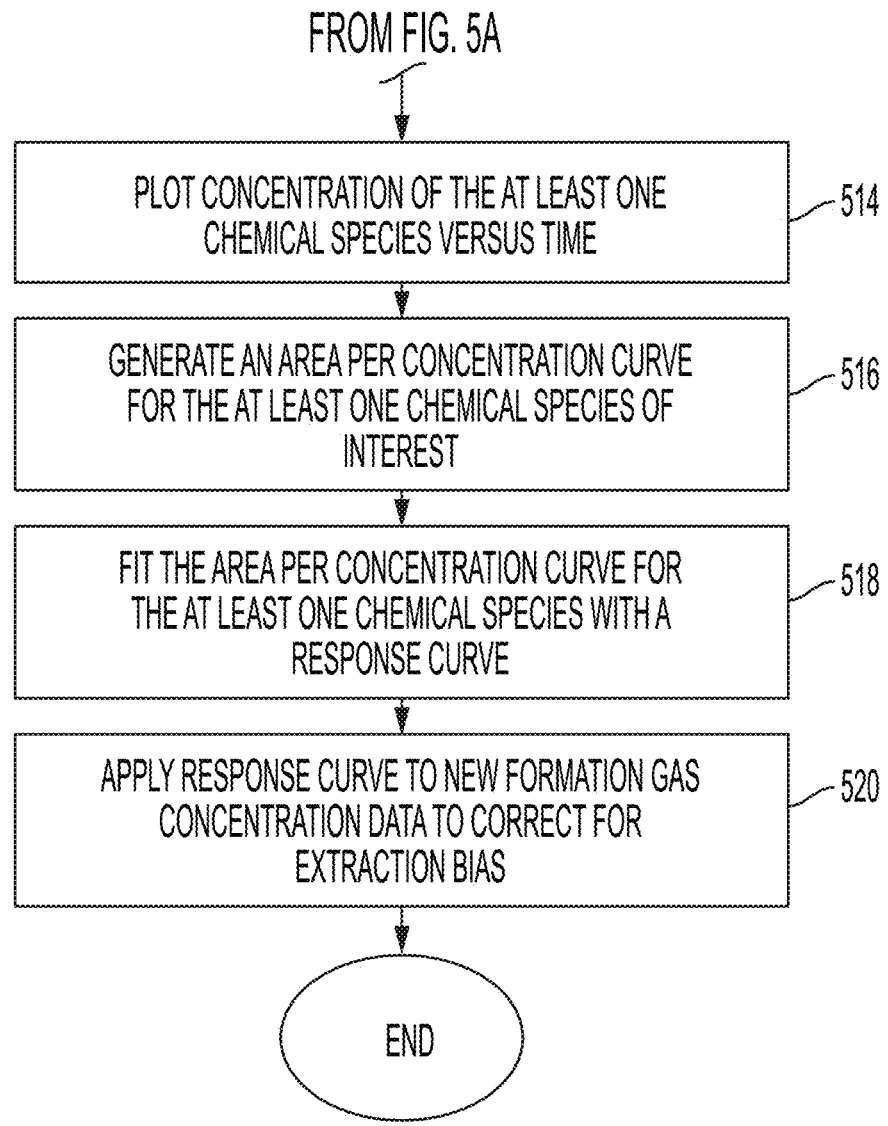

FIGS. 5A and 5B illustrate a flowchart depicting an additional process 500 for drilling fluid sampling and gas extraction and analysis, according to some examples of the present disclosure. Operations of the process 500 may be performed by software, firmware, hardware or a combination thereof. The operations of the flowchart start at block 502.

At block 502, the process 500 involves receiving a drilling fluid sample in an extraction vessel. The drilling fluid sample can represent a drilling fluid that will be used during a drilling operation such as depicted and described in FIG. 1. In some examples of the present disclosure, the extraction vessel can be a 20 liter extraction vessel with a maintained headspace.

At block 504, the process 500 involves flushing the drilling fluid sample with a hydrocarbon blend representing at least one chemical species of interest. A flushed drilling fluid sample can be generated. In some examples, the drilling fluid sample can be flushed by bubbling through the drilling fluid sample. The hydrocarbon blend can include methane, ethane, propane, iso-butane, n-butane, iso-pentane, n-pentane, ethylene, propylene, or any suitable combination of the foregoing in known concentrations.

At block 506, the process 500 involves closing the extraction vessel and maintaining the extraction vessel temperature at room temperature for a predetermined amount of time. Maintaining the extraction vessel at room temperature for a predetermined amount of time can allow the flushed drilling fluid sample to come to equilibrium. In some examples of the present disclosure, the predetermined amount of time is at least thirty minutes.

At block 508, the process 500 involves connecting the extraction vessel to a constant volume/constant temperature (CVCT) gas extractor with a maintained headspace. The CVCT gas extractor can be connected to a gas chromatograph. The gas chromatograph can be set up for gas concentration measurement and other analysis. In some examples, the extraction vessel can be connected to the CVCT prior to receiving the drilling fluid sample.

At block 510, the process 500 involves opening the extraction vessel. The flushed drilling fluid sample can be allowed to flow or be withdrawn from the CVCT gas extractor. In some examples of the present disclosure, the CVCT gas extractor can be maintained at a predetermined extraction temperature.

At block 512, the process 500 involves flowing a carrier gas through the headspace of the vessel and determining a concentration of at least one chemical species of interest using the gas chromatograph. The carrier gas can aid the movement of extracted gas toward the gas chromatograph through a gas outlet. For example, with reference to FIG. 3, the gas chromatograph 308 can determine concentration of each chemical species of the extracted dissolved gas over time received from the gas extraction and sampling system 306.

At block 514, the process 500 involves plotting a concentration of each chemical species versus time. For example, with reference to FIG. 3, the computing device 165 may receive the concentration of each chemical species from the gas chromatograph 308 and plot a concentration of each chemical species versus time. To illustrate, FIG. 6 depicts a graph 600 of propane concentration in parts per million (PPM) along the Y-axis and time in seconds along the X-axis.

At block 516, the process 500 involves generating an area per concentration curve for each chemical species. For example, with reference to FIG. 3, the computing device 165 can generate an area per concentration curve for each chemical species based on the concentration over time curves generated for each species such as the curve depicted in FIG. 6. In some examples of the present disclosure, a total concentration per time value is generated by integrating the area under a concentration over time curve at each of a series of points in time. In this manner, the integration generates area under the curve data by calculating an area under the curve each time point. Results of an integration can be displayed using an area per concentration curve. The area per concentration curve can include total concentration per time point on the Y-axis and instantaneous concentration values directly measured for each time point on the X-axis.

At block 518, the process 500 involves fitting the area per concentration curve for each chemical species with a response curve. For example, with reference to FIG. 3, the computing device 165 can fit the area per concentration with a response curve for each chemical species. A best fitted curve can be selected. For example, the fitted curve can be power log, polynomial, logarithmic, exponential, etc.

At block 520, the process 500 involves applying the response curve to original values of concentration of each chemical species to create corrected values of concentration of each chemical species to correct for system bias. For example, with reference to FIG. 3, the computing device 165 may apply the response curve to original values of concentration of each chemical species to create corrected values of concentration of each chemical species to correct for system bias. For example, the fitted curve can be represented as an equation in which a new value is defined as a function of a previously determined value. So, each point in time of the raw data can be adjusted based on the equation defined by the fitted curve.

Figure 12:
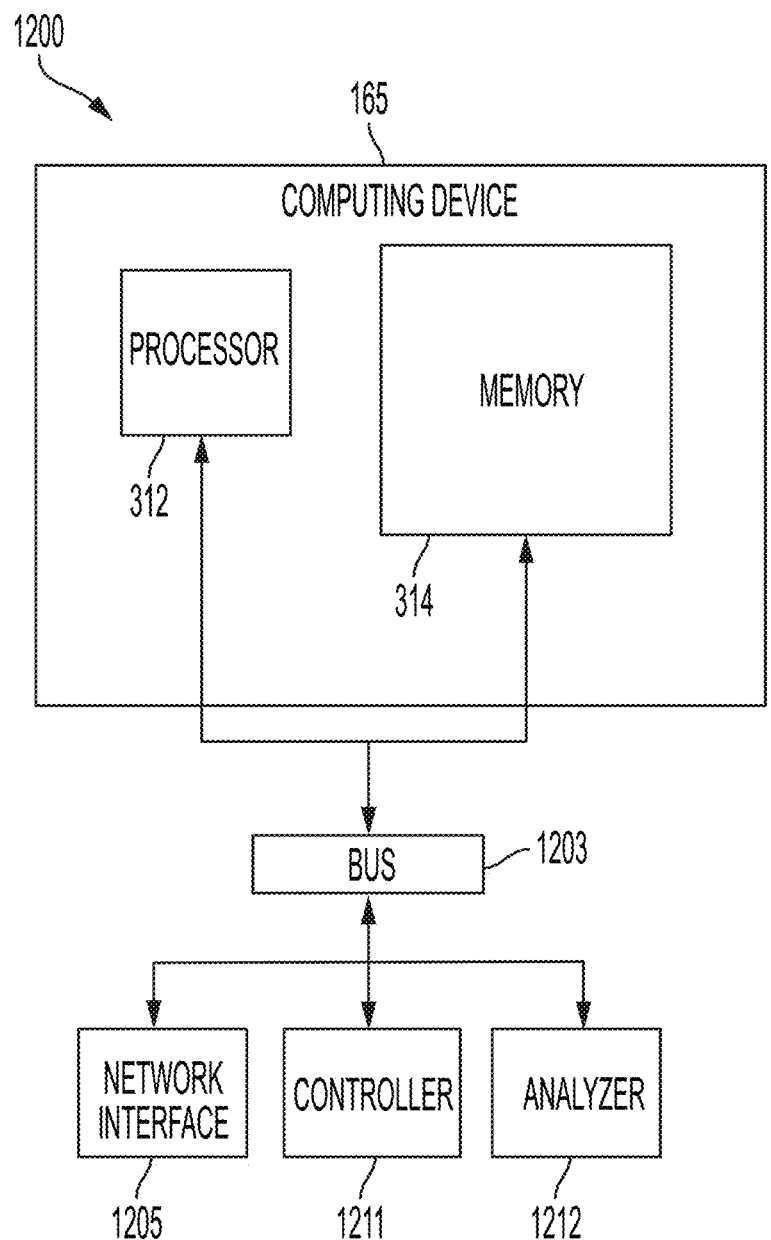
FIG. 12 is a block diagram depicting an example computer, according to one example of the present disclosure.

FIG. 12 depicts an example computer, according to some examples of the present disclosure. The computer includes a processor 312 (possibly including multiple processors, multiple cores, multiple nodes, or implementing multi-threading, etc.) The computer includes a memory 314. The memory 314 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 1203 (e.g., PCI, ISA, PCI-Express, HyperTransport® bus, InfiniBand® bus, NuBus, etc.) and a network interface 1205 (e.g., a Fiber Channel interface, an Ethernet interface, an internet small computer system interface, SONET interface, wireless interface, etc.).

The computer also includes an analyzer 1212 and a controller 1211. The analyzer 1212 can perform processing and analyzing of a flushed drilling fluid sample (as described above). The controller 1211 can control the different operations that can occur in the response to results from the analysis. For example, the controller 1211 can communicate instructions to the appropriate equipment, devices, etc. to alter different hydrocarbon recovery operations. Any one of the previously described functionalities may be partially (or entirely) implemented in hardware or on the processor 312. For example, the functionality may be implemented with an application specific integrated circuit, in logic implemented in the processor 312, in a co-processor on a peripheral or card, etc. Further, realizations may include fewer or additional components not illustrated in FIG. 12 (e.g., video cards, audio cards, additional network interfaces, peripheral devices etc.). The processor 312 and the network interface 1205 are coupled to the bus 1203. Although illustrated as being coupled to the bus 1203, the memory 314 may be coupled to the processor 312.

As will be appreciated, aspects of the present disclosure may be depicted as a system, method or program code/instructions stored in one or more machine-readable media. Accordingly, aspects may take the form of hardware, software (including firmware, resident software, micro-code, etc.), or a combination of software and hardware aspects that may generally be referred to herein as a "circuit", "module" or "system". The functionality presented as individual modules/units in the example illustrations can be organized differently in accordance with any one of platform (operating system or hardware), application ecosystem, interfaces, programmer preferences, programming language, administrator preferences, etc.

Any combination of one or more machine readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain or store a program for use by or in connection with an instruction execution system, apparatus, or device. A machine-readable storage medium is not a machine-readable signal medium.

A machine-readable signal medium may include propagated data signal with machine-readable program code depicted therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code depicted on a machine-readable medium may be transmitted using an appropriate medium, including but not limited to wireless, wireline, optical fiber cable, RF, etc., or any suitable combination of the foregoing. Computer program code for carrying out operations for aspects of the disclosure may be written in any combination of one or more programming languages, including an object oriented programming language such as Java® programming language, C++ or the like; a dynamic programming language such as Python; a scripting language such as Perl programming language or PowerShell script language; and conventional procedural programming languages, such as the "C" programming language or similar programming languages. The program code may execute in a distributed manner across multiple machines and may execute on one machine while providing results or accepting input on another machine.

Using the apparatus, systems, and methods disclosed herein may provide the ability to monitor changes in wellbore particles (e.g., cuttings), so that the impact of drilling fluid properties and activities in the field can be assessed immediately. This ability may be used to increase efficiency by redirecting pumping and drilling operations in real-time, perhaps as part of a closed-loop control system. While the aspects of the disclosure are described with reference to various implementations and exploitations, it will be understood that these aspects are illustrative and that the scope of the claims is not limited to them. In general, techniques for processing and analyzing of particles from wellbore operations as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary. Particular operations are illustrated in the context of specific illustrative examples. Other allocations of functionality are envisioned and may fall within the scope of the disclosure. Use of the phrase "at least one of" preceding a list with the conjunction "and" should not be construed as a list of categories with one item from each category, unless specifically stated otherwise. A clause that recites "at least one of A, B, and C" can be infringed with only one of the listed items, multiple of the listed items, and one or more of the items in the list and another item not listed.

In some aspects, methods and systems for gas extraction and sampling bias correction are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a method, comprising: controlling a gas extraction and sampling system to flush a drilling fluid sample with a hydrocarbon blend with a determined concentration of at least one chemical species to generate a flushed drilling fluid sample; controlling the gas extraction and sampling system to extract a dissolved gas from the flushed drilling fluid sample; determining a concentration over time of at least one chemical species of the dissolved gas; generating an area per concentration curve based on the concentration over time of the at least one chemical species; determining at least one concentration value of the at least one chemical species of the dissolved gas from the flushed drilling fluid sample; modifying the at least one concentration value based on the area per concentration curve; and correcting bias caused by the gas extraction and sampling system during subsequent gas extraction and sampling system operations using the at least one modified concentration value.

Example 2 is the method of example 1, further comprising: stirring the drilling fluid sample while flushing the drilling fluid sample with the hydrocarbon blend.

Example 3 is the method of examples 1-2, wherein flushing the drilling fluid sample with the hydrocarbon blend comprises bubbling gas through the drilling fluid sample.

Example 4 is the method of examples 1-3, further comprising: flushing a headspace of a vessel containing the flushed drilling fluid sample with air, nitrogen, or other non-reactive gas while maintaining the flushed drilling fluid sample at room temperature.

Example 5 is the method of examples 1-4, further comprising: stirring the flushed drilling fluid sample while maintaining the flushed drilling fluid sample at room temperature.

Example 6 is the method of examples 1-5, further comprising: prior to generating an area per concentration curve, heating a vessel holding the flushed drilling fluid sample to a predetermined extraction temperature.

Example 7 is the method of examples 1-6, wherein determining a concentration over time of at least one chemical species further comprises flowing a carrier gas through a headspace of a vessel holding the flushed drilling fluid sample to aid in movement of extracted gases to a gas outlet.

Example 8 is the method of examples 1-7, wherein modifying the at least one concentration value comprises: fitting the area per concentration curve with a response curve; and applying the response curve to a determined concentration.

Example 9 is the method of example 8, wherein correcting the bias comprises generating a corrected concentration of each species based on applying the response curve to the determined concentration.

Example 10 is a system, comprising: a gas extraction and sampling system positionable to: flush a drilling fluid sample with a hydrocarbon blend with a determined concentration of at least one chemical species to generate a flushed drilling fluid sample; maintain the flushed drilling fluid sample at room temperature for a predetermined amount of time; and extract a dissolved gas from the flushed drilling fluid sample; a gas chromatograph connectable to the gas extraction and sampling system to determine a concentration over time of at least one chemical species of the dissolved gas; a processor; and a memory that includes instructions executable by the processor for causing the processor to: generate an area per concentration curve based on the concentration over time of the at least one chemical species of the dissolved gas; determine at least one concentration value of the at least one chemical species of the dissolved gas; modify the at least one concentration value based on the area per concentration curve; and correct bias caused by the gas extraction and sampling system during subsequent gas extraction and sampling system operations using the at least one modified concentration value.

Example 11 is the system of example 10, wherein the gas extraction and sampling system comprises a 20 liter extraction vessel and a constant volume/constant temperature gas extractor (CVCT), wherein the 20 liter extraction vessel connectable to the CVCT.

Example 12 is the system of examples 10-11, wherein the gas extraction and sampling system is further positionable to stir the drilling fluid sample while flushing the drilling fluid sample with the hydrocarbon blend.

Example 13 is the system of examples 10-12, wherein the gas extraction and sampling system is further positionable to flush the drilling fluid sample with a hydrocarbon blend by bubbling gas through the drilling fluid sample.

Example 14 is the system of examples 10-13, wherein the memory further comprises instructions executable by the processor for causing the processor to modify the at least one concentration value by: fitting the area per concentration curve with a response curve; and applying the response curve to the determined concentration.

Example 15 is the system of examples 10-14, wherein the memory further comprises instructions executable by the processor for causing the processor to: determine a fluid formation characteristic of a subterranean formation using at least one modified concentration value; and modify a hydrocarbon recovery operation based on a determined fluid formation characteristic.

Example 16 is a non-transitory computer-readable medium comprising instructions that are executable by a processor for causing the processor to perform operations comprising: determining a concentration over time of at least one chemical species of a dissolved gas extracted from a flushed drilling fluid sample; generating an area per concentration curve based on the concentration over time of the at least one chemical species; determining at least one concentration value of the at least one chemical species of the dissolved gas in the flushed drilling fluid sample; modifying the at least one concentration value based on the area per concentration curve; and correcting bias caused by a gas extraction and sampling system during subsequent gas extraction and sampling system operations using the at least one modified concentration value.

Example 17 is the non-transitory computer-readable medium of example 16, wherein modifying the at least one concentration value comprises: fitting the area per concentration curve with a response curve; and applying the response curve to a determined concentration.

Example 18 is the non-transitory computer-readable medium of example 17, wherein modifying the at least one concentration value further comprises generating a corrected concentration of the at least one chemical species based on applying the response curve to a determined concentration.

Example 19 is the non-transitory computer-readable medium of examples 16-18, wherein fitting the area per concentration curve with a response curve comprises generating the response curve based on the area per concentration curve.

Example 20 is the non-transitory computer-readable medium of examples 16-19, further comprising instructions that are executable by the processor for causing the processor to: determine a fluid formation characteristic of a subterranean formation using the at least one modified concentration value; and modify a hydrocarbon recovery operation based on a determined fluid formation characteristic.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method, comprising:
controlling a gas extraction and sampling system to flush a drilling fluid sample with a hydrocarbon blend with a determined concentration of at least one chemical species to generate a flushed drilling fluid sample;
controlling the gas extraction and sampling system to extract a dissolved gas from the flushed drilling fluid sample;
determining a concentration over time of at least one chemical species of the dissolved gas;
generating an area per concentration curve based on the concentration over time of the at least one chemical species;
determining at least one concentration value of the at least one chemical species of the dissolved gas from the flushed drilling fluid sample;
modifying the at least one concentration value based on the area per concentration curve; and
correcting bias caused by the gas extraction and sampling system during subsequent gas extraction and sampling system operations using the at least one modified concentration value.

2. The method of claim 1, further comprising:
stirring the drilling fluid sample while flushing the drilling fluid sample with the hydrocarbon blend.

3. The method of claim 1, wherein flushing the drilling fluid sample with the hydrocarbon blend comprises bubbling gas through the drilling fluid sample.

4. The method of claim 1, further comprising:
flushing a headspace of a vessel containing the flushed drilling fluid sample with air, nitrogen, or other non-reactive gas while maintaining the flushed drilling fluid sample at room temperature.

5. The method of claim 1, further comprising:
stirring the flushed drilling fluid sample while maintaining the flushed drilling fluid sample at room temperature.

6. The method of claim 1, further comprising:
prior to generating an area per concentration curve, heating a vessel holding the flushed drilling fluid sample to a predetermined extraction temperature.

7. The method of claim 1, wherein determining a concentration over time of at least one chemical species further comprises flowing a carrier gas through a headspace of a vessel holding the flushed drilling fluid sample to aid in movement of extracted gases to a gas outlet.

8. The method of claim 1, wherein modifying the at least one concentration value comprises:
fitting the area per concentration curve with a response curve; and
applying the response curve to a determined concentration.

9. The method of claim 8, wherein correcting the bias comprises generating a corrected concentration of each species based on applying the response curve to the determined concentration.

10. A system, comprising:
a gas extraction and sampling system positionable to:
flush a drilling fluid sample with a hydrocarbon blend with a determined concentration of at least one chemical species to generate a flushed drilling fluid sample;
maintain the flushed drilling fluid sample at room temperature for a predetermined amount of time; and
extract a dissolved gas from the flushed drilling fluid sample;
a gas chromatograph connectable to the gas extraction and sampling system to determine a concentration over time of at least one chemical species of the dissolved gas;
a processor; and
a memory that includes instructions executable by the processor for causing the processor to:
generate an area per concentration curve based on the concentration over time of the at least one chemical species of the dissolved gas;
determine at least one concentration value of the at least one chemical species of the dissolved gas;
modify the at least one concentration value based on the area per concentration curve; and
correct bias caused by the gas extraction and sampling system during subsequent gas extraction and sampling system operations using the at least one modified concentration value.

11. The system of claim 10, wherein the gas extraction and sampling system comprises a 20 liter extraction vessel and a constant volume/constant temperature gas extractor (CVCT), wherein the 20 liter extraction vessel connectable to the CVCT.

12. The system of claim 10, wherein the gas extraction and sampling system is further positionable to stir the drilling fluid sample while flushing the drilling fluid sample with the hydrocarbon blend.

13. The system of claim 10, wherein the gas extraction and sampling system is further positionable to flush the drilling fluid sample with a hydrocarbon blend by bubbling gas through the drilling fluid sample.

14. The system of claim 10, wherein the memory further comprises instructions executable by the processor for causing the processor to modify the at least one concentration value by:
fitting the area per concentration curve with a response curve; and
applying the response curve to the determined concentration.

15. The system of claim 10, wherein the memory further comprises instructions executable by the processor for causing the processor to:
determine a fluid formation characteristic of a subterranean formation using at least one modified concentration value; and
modify a hydrocarbon recovery operation based on a determined fluid formation characteristic.

16. A non-transitory computer-readable medium comprising instructions that are executable by a processor for causing the processor to perform operations comprising:
determining a concentration over time of at least one chemical species of a dissolved gas extracted from a flushed drilling fluid sample;
generating an area per concentration curve based on the concentration over time of the at least one chemical species;
determining at least one concentration value of the at least one chemical species of the dissolved gas in the flushed drilling fluid sample;
modifying the at least one concentration value based on the area per concentration curve; and correcting bias caused by a gas extraction and sampling system during subsequent gas extraction and sampling system operations using the at least one modified concentration value.

17. The non-transitory computer-readable medium of claim 16, wherein modifying the at least one concentration value comprises:
   fitting the area per concentration curve with a response curve; and
   applying the response curve to a determined concentration.

18. The non-transitory computer-readable medium of claim 17, wherein modifying the at least one concentration value further comprises generating a corrected concentration of the at least one chemical species based on applying the response curve to a determined concentration.

19. The non-transitory computer-readable medium of claim 17, wherein fitting the area per concentration curve with a response curve comprises generating the response curve based on the area per concentration curve.

20. The non-transitory computer-readable medium of claim 16, further comprising instructions that are executable by the processor for causing the processor to:
   determine a fluid formation characteristic of a subterranean formation using the at least one modified concentration value; and
   modify a hydrocarbon recovery operation based on a determined fluid formation characteristic.

* * * * *